(12) United States Patent
Chossade

(10) Patent No.: US 8,846,033 B2
(45) Date of Patent: Sep. 30, 2014

(54) DIETARY SUPPLEMENT

(75) Inventor: Christian Chossade, Morton (FR)

(73) Assignee: ET & DS Company Ltd., Limassol (CY)

( * ) Notice: Subject to any disclaimer, the term of this patent is extended or adjusted under 35 U.S.C. 154(b) by 867 days.

(21) Appl. No.: 12/452,759

(22) PCT Filed: Jun. 16, 2008

(86) PCT No.: PCT/FR2008/051071
§ 371 (c)(1),
(2), (4) Date: Jan. 21, 2010

(87) PCT Pub. No.: WO2009/004238
PCT Pub. Date: Jan. 8, 2009

(65) Prior Publication Data
US 2010/0143320 A1    Jun. 10, 2010

(30) Foreign Application Priority Data
Jun. 18, 2007 (EP) .................... 07360026

(51) Int. Cl.
*A61K 38/54* (2006.01)
*A61P 1/14* (2006.01)
*A23L 1/305* (2006.01)

(52) U.S. Cl.
CPC ......... *A23L 1/305* (2013.01); *C12Y 302/01108* (2013.01); *C12Y 304/22033* (2013.01); *C12Y 302/01001* (2013.01); *A23L 1/3055* (2013.01); *A23L 1/3056* (2013.01)

USPC ........................................... 424/94.2

(58) Field of Classification Search
None
See application file for complete search history.

(56) References Cited

U.S. PATENT DOCUMENTS

| 4,079,125 | A |   | 3/1978 | Sipos |
|---|---|---|---|---|
| 5,260,074 | A | * | 11/1993 | Sipos ........................... 424/497 |
| 5,569,458 | A |   | 10/1996 | Greenberg |
| 5,902,617 | A |   | 5/1999 | Pabst |
| 2003/0059498 | A1 | * | 3/2003 | Apajalahti et al. .............. 426/62 |
| 2004/0253295 | A1 |   | 12/2004 | Martin et al. |
| 2005/0112176 | A1 | * | 5/2005 | Dopson et al. ................ 424/439 |
| 2006/0280840 | A1 | * | 12/2006 | Robertson ...................... 426/72 |

FOREIGN PATENT DOCUMENTS

WO  WO 2006/060414 A2  6/2006
WO  WO 2007/053619 A2  5/2007

OTHER PUBLICATIONS

International Search Report for International Application No. PCT/FR2008/051071, issued Feb. 11, 2009.

* cited by examiner

*Primary Examiner* — Lisa J Hobbs
(74) *Attorney, Agent, or Firm* — Oliff PLC

(57) ABSTRACT

The invention relates to a dietary supplement that promotes proper ingestion and proper digestion of animal and/or vegetable proteins. The supplement comprises an enzyme mixture containing amylase, lactase and bromelain in the following dosage by weight: 15 mg to 90 mg amylase, 18 mg to 90 mg lactase and 6 mg to 80 mg bromelain.

20 Claims, No Drawings

DIETARY SUPPLEMENT

The present invention relates to digestion essentially of milk proteins, but also to other proteins absorbed in a large amount and repeatedly. It relates to a dietary supplement promoting proper ingestion and proper digestion of animal and/or vegetable proteins, and consisting of a mixture of enzymes comprising amylase, lactase and bromelain.

Digestion of milk protein in particular poses a problem in many respects. Thus, certain persons are unable to retain within their body a particular enzyme, lactase which is used for digesting lactose contained in dairy products. In fact they are intolerant to lactose. When these persons consume dairy products, they suffer from ailments, such as vomiting, flatulence, halitosis, cramps or other intestinal disorders of the diarrhea type, etc.

In fact, lactase is deficient in a large portion of the world adult population. This enzyme, present in newborns for digesting maternal milk, gradually disappears after weaning. Continued consumption of milk amounts to maintaining the lactase slightly active, but this is going against nature. The production is forced of an enzyme in principle intended to disappear.

Under the assumption of a lack of congenital or acquired lactase production, the subject is therefore intolerant to lactose, intolerance resulting from a reaction of the body to consumed milk.

Lactase belongs to the brush-border of enterocytes, which are the cells making up the wall of the intestine. Now, when the activity of the lactase is insufficient, lactose accumulates and passes into the large intestine where it is fermented by colic flora, in the same way as other absorbed proteins, either in large amounts or without lipids and/or carbohydrates. This causes the symptoms described above. Insufficient production of lactase by the body in addition to the consequences described above, may also generate more serious disorders.

It is therefore not sufficient to supplement the body with lactase in order to avoid the digestive disorders described above, since a poorly dosed provision over a too long period generates other risks, for example poor blood circulation.

With reference to the problem related to digestion which is solved by the invention, amylase—the second constituent of the invention—is an enzyme, notably with which starch and dextrins may be digested by transforming them into assimilable reducing sugars. It is secreted by the pancreas and salivary glands. It is possible to increase the amount of amylase in the organism when either one of these glands is defective.

One of the major benefits in the perspective of promoting digestion is that it increases the amount of saliva in the mouth and the work of reducing the foodstuffs may thereby be started. It avoids the "dead weight" feeling due to ingested proteins.

A too large absorption of amylase however results in an abnormal increase in the level of triglycerides. This may cause chronic pancreatitises, cholecystitises, cysts, ulcer perforations of the duodenum or peritonitises, notably in the case of absorption of animal enzymes. Its dosage is therefore important.

Always in the same digestive perspective, the third constituent of the dietary supplement of the invention, bromelain moreover known and used in treating venous diseases, contusions, arthritis, rheumatoid arthritis, and gout, also allows total reduction of proteins and of its components, by however acting less rapidly than lactose and amylase. Therefore it completes their action. It is also used in Europe for promoting recovery after an operation or sports injuries or for treating sinusitises or phlebitises.

At a high dose, it however causes secondary effects such as vomiting and severe kidney failure, and its dosage should therefore be measured with great care.

The object of the invention aims at producing a dietary supplement ensuring proper buccal absorption on the one hand and digestion without any disorders on the other hand, while however avoiding potential secondary effects due to its constituents.

In other words, the dietary supplement of the invention should promote proper ingestion and proper digestion of animal and/or vegetable proteins. For this purpose, according to the invention, the mixture of enzymes based on the combination of amylase, lactase and bromelain, should observe the following weight dosage:

15 mg-90 mg for amylase,
18 mg-90 mg for lactase; and
6 mg-80 mg for bromelain.

The use of these enzymes is mainly of interest insofar that it may accelerate chemical and biochemical reactions which occur during digestion. These enzymes thus have the role of a catalyst in the human body.

The dietary supplement of the invention is indicated in the case of difficulties related to digestion of any type of proteins, regardless of the vegetable or animal origin of the latter. First, it allows an increase in the lactase content of the body for the purposes of proper digestion, but also allows different placement in the mouth (buccal ingestion of foodstuff) by associating lactase with amylase.

Finally, association of bromelain with amylase and with lactase promotes digestion without any bothersome or undesired secondary effects. Dosage of lactase is particularly important because with such a dosage which may be described as being a low as possible in order to avoid detrimental effects on the blood stream, even in the case of ingestion over a long period. Secondary effects possibly caused by a high dosage of lactase are thereby avoided.

With the aforementioned dosage of amylase, between 15 and 90 mg, it is also possible to avoid any risk of complication related to prolonged taking, while providing the previously explained contribution to digestion of proteins.

The use of bromelain, in an amount between 6 mg and 80 mg, may provide a significant benefit to digestion and does not generate any secondary effect in the case of ingestion over a long period.

Many applications of the dietary supplement of the invention are possible.

Thus, according to one example, for a dietary supplement notably intended for sports(wo)men, the amounts of the different enzymes may more specifically be:

30 mg for amylase,
40 mg for lactase; and
15 mg for bromelain.

For another application intended for a more dietetic use, the provided amounts are of the order of:

40 mg for amylase,
60 mg for lactase; and
25 mg for bromelain.

According to the invention, the dietary supplement either added or not to other ingredients, may appear in all the possible galenic forms, i.e.: powder or granules to be re-hydrated or to be consumed as such, pills, tablets, gelatin capsules, but also in a liquid or pasty presentation. These forms or presentations are not exhaustive.

Moreover, the invention relates to a concentrated protein food product, supplemented by means of a dietary supplement as shown above. Preferably, said protein concentrate has a protein content greater than 82%.

Digestion of hyperprotein foodstuffs of any type may be facilitated by such a concentrated and supplemented food product. The latter secondarily promotes draining and elimination of fats in sports(wo)men, as well as enrichment of the muscular mass.

Moreover, spectacular results may be obtained for resorbing fats in obese persons.

In such a product, the concentrated proteins may be of animal origin. According to an alternative, they may also be of vegetable origin or further result from a mixture of both.

Preferably, according to the invention, an amylase of vegetable origin and a lactase of vegetable and/or animal origin are used.

According to the conducted tests, by associating amylase, lactase and bromelain with dosages comprised in the intervals indicated earlier, i.e. 15-90 mg for amylase, 18-90 mg for lactase and 6-80 mg for bromelain, a significant and reliable result in improving digestion of proteins may be obtained. The association of these dosages—which may be described as low—of enzymes is therefore unexpectedly, particularly indicated in the treatment of digestive problems.

The results related to the association of these three enzymes at a low dosage are all the more remarkable since their use was hitherto known only at strong or high dosages for obtaining a significant result in digestion, with the risk of bothersome, secondary effects, or even dangerous effects in certain cases. The particularly interesting results obtained in digestion of proteins cannot in any case be observed with taking any one of the previous enzymes individually with a dosage as indicated.

An undeniable advantage of the dietary supplement according to the invention therefore lies for a large part in the interaction of amylase, lactase and bromelain, each with a low dose.

The invention claimed is:

1. A concentrated protein dietary product, supplemented by means of a dietary supplement, comprising:
    a concentrated protein food product having a protein content greater than 82%; and
    a dietary supplement promoting proper ingestion and proper digestion of animal and/or vegetable proteins added to the concentrated protein food product, the dietary supplement consisting of a mixture of enzymes consisting essentially of amylase, lactase, and bromelain,
    wherein the weight dosage of amylase, lactase, and bromelain is:
        15 mg to 90 mg for amylase,
        18 mg to 90 mg for lactase, and
        6 mg to 80 mg for bromelain.

2. The concentrated protein dietary product according to claim 1, wherein the proteins of the concentrated protein food product are of animal origin.

3. The concentrated protein dietary product according to claim 1, wherein the proteins of the concentrated protein food product are of vegetable origin.

4. The concentrated protein dietary product according to claim 1, wherein the weight dosage of amylase, lactase, and bromelain is:
    30 mg for amylase,
    40 mg for lactase, and
    15 mg for bromelain.

5. The concentrated protein dietary product according to claim 1, wherein the weight dosage of amylase, lactase, and bromelain is:
    40 mg for amylase,
    60 mg for lactase, and
    25 mg for bromelain.

6. The concentrated protein dietary product according to claim 1, wherein the concentrated protein dietary product is added to a hyperprotein foodstuff.

7. A supplemented dietary product comprising:
    a dietary product containing animal and/or vegetable proteins; and
    a dietary supplement promoting proper ingestion and proper digestion of animal and/or vegetable proteins added to the dietary product, the dietary supplement consisting of a mixture of enzymes consisting essentially of amylase, lactase, and bromelain,
    wherein the weight dosage of amylase, lactase, and bromelain is:
        15 mg to 90 mg for amylase,
        18 mg to 90 mg for lactase, and
        6 mg to 80 mg for bromelain.

8. The supplemented dietary product of claim 7, wherein the weight dosage of amylase, lactase, and bromelain is:
    30 mg for amylase,
    40 mg for lactase, and
    15 mg for bromelain.

9. The supplemented dietary product of claim 7, wherein the weight dosage of amylase, lactase, and bromelain is:
    40 mg for amylase,
    60 mg for lactase, and
    25 mg for bromelain.

10. The supplemented dietary product of claim 7, wherein the proteins are of animal origin.

11. The supplemented dietary product of claim 7, wherein the proteins are of vegetable origin.

12. A method of promoting proper ingestion and proper digestion of animal and/or vegetable proteins, the method comprising ingesting the supplemented dietary product of claim 7.

13. The method of promoting proper ingestion and proper digestion of animal and/or vegetable proteins according to claim 12, wherein the weight dosage of amylase, lactase, and bromelain is:
    30 mg for amylase,
    40 mg for lactase, and
    15 mg for bromelain.

14. The method of promoting proper ingestion and proper digestion of animal and/or vegetable proteins according to claim 12, wherein the weight dosage of amylase, lactase, and bromelain is:
    40 mg for amylase,
    60 mg for lactase, and
    25 mg for bromelain.

15. The method of promoting proper ingestion and proper digestion of animal and/or vegetable proteins according to claim 12, wherein the proteins are of animal origin.

16. The method of promoting proper ingestion and proper digestion of animal and/or vegetable proteins according to claim 12, wherein the proteins are of vegetable origin.

17. A concentrated protein dietary product, supplemented by means of a dietary supplement, comprising:
    a concentrated protein food product having a protein content greater than 82%; and
    a dietary supplement promoting proper ingestion and proper digestion of animal and/or vegetable proteins added to the concentrated protein food product, the dietary supplement consisting of a mixture of enzymes comprising amylase, lactase, and bromelain,
wherein the weight dosage of amylase, lactase, and bromelain is:
15 mg to 30 mg for amylase,
18 mg to 90 mg for lactase, and
6 mg to 80 mg for bromelain.

18. The concentrated protein dietary product according to claim 17, wherein the weight dosage of amylase, lactase, and bromelain is:
30 mg for amylase,
40 mg for lactase, and
15 mg for bromelain.

19. A method of promoting proper ingestion and proper digestion of animal and/or vegetable proteins, the method comprising ingesting the concentrated protein dietary product of claim 17.

20. The concentrated protein dietary product according to claim 17, wherein the concentrated protein dietary product is added to a hyperprotein foodstuff.

\* \* \* \* \*